(12) United States Patent
Kanazawa

(10) Patent No.: US 10,026,991 B2
(45) Date of Patent: Jul. 17, 2018

(54) MANUFACTURING METHOD FOR AMINO-SUBSTITUTED PHOSPHAZENE COMPOUND, MANUFACTURING METHOD FOR ELECTROLYTE SOLUTION FOR NONAQUEOUS SECONDARY BATTERY, AND MANUFACTURING METHOD FOR NONAQUEOUS SECONDARY BATTERY

(71) Applicant: FUJIFILM Corporation, Tokyo (JP)

(72) Inventor: Yoshinori Kanazawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/395,491

(22) Filed: Dec. 30, 2016

(65) Prior Publication Data

US 2017/0110758 A1    Apr. 20, 2017

Related U.S. Application Data

(63) Continuation of application No. PCT/JP2015/068947, filed on Jul. 1, 2015.

(30) Foreign Application Priority Data

Jul. 4, 2014 (JP) ................................. 2014-138947

(51) Int. Cl.
*C07F 9/6593* (2006.01)
*C07F 9/6581* (2006.01)
(Continued)

(52) U.S. Cl.
CPC ..... *H01M 10/0564* (2013.01); *C07F 9/65815* (2013.01); *C07F 9/65817* (2013.01);
(Continued)

(58) Field of Classification Search
None
See application file for complete search history.

(56) References Cited

U.S. PATENT DOCUMENTS 4,223,133 A * 9/1980 Bunnell ............... C07D 499/00
540/215
5,830,600 A 11/1998 Narang et al.
(Continued)

FOREIGN PATENT DOCUMENTS

CN 1680380 A 10/2005
CN 101410359 A 4/2009
(Continued)

OTHER PUBLICATIONS

Harada, JP2009235009 Machine Translation; 75 pages total.*
(Continued)

*Primary Examiner* — Ula C Ruddock
*Assistant Examiner* — Anna Korovina
(74) *Attorney, Agent, or Firm* — Birch, Stewart, Kolasch & Birch, LLP

(57) ABSTRACT

Provided are a manufacturing method for an amino-substituted phosphazene compound including reacting a fluorinated phosphazene compound and an amine compound in presence of a compound having a fluorine trapping function; and synthesizing a compound obtained by substituting the amine compound for the fluorinated phosphazene compound, a manufacturing method for an electrolyte solution for a nonaqueous secondary battery using this, and a manufacturing method for a nonaqueous secondary battery.

8 Claims, 2 Drawing Sheets

¹H-NMR SPECTRUM OF COMPOUND 1-1

(51) Int. Cl.
*H01M 10/0525* (2010.01)
*H01M 10/0561* (2010.01)
*H01M 10/0564* (2010.01)
*H01M 10/058* (2010.01)
*H01M 4/131* (2010.01)
*H01M 4/525* (2010.01)
*H01M 4/505* (2010.01)
*H01M 4/583* (2010.01)
*H01M 4/58* (2010.01)
*H01M 4/56* (2006.01)
*H01M 4/48* (2010.01)
*H01M 4/62* (2006.01)
*H01M 4/66* (2006.01)
*H01M 2/16* (2006.01)

(52) U.S. Cl.
CPC ....... *H01M 2/1613* (2013.01); *H01M 2/1626* (2013.01); *H01M 4/131* (2013.01); *H01M 4/483* (2013.01); *H01M 4/505* (2013.01); *H01M 4/525* (2013.01); *H01M 4/56* (2013.01); *H01M 4/583* (2013.01); *H01M 4/5815* (2013.01); *H01M 4/623* (2013.01); *H01M 4/625* (2013.01); *H01M 4/626* (2013.01); *H01M 4/662* (2013.01); *H01M 4/669* (2013.01); *H01M 10/058* (2013.01); *H01M 10/0525* (2013.01); *H01M 10/0561* (2013.01); *H01M 2300/002* (2013.01); *H01M 2300/0037* (2013.01)

(56) References Cited

U.S. PATENT DOCUMENTS

| | | |
|---|---|---|
| 2004/0191635 A1 | 9/2004 | Otsuki et al. |
| 2006/0074264 A1 | 4/2006 | Ito et al. |
| 2009/0054687 A1* | 2/2009 | Ikeda .................. C08G 65/007 562/849 |
| 2009/0170983 A1* | 7/2009 | Tada .................. C07F 9/65815 524/95 |
| 2010/0292516 A1 | 11/2010 | Sugimoto |
| 2013/0295470 A1 | 11/2013 | Shatunov et al. |
| 2014/0178752 A1 | 6/2014 | Park et al. |

FOREIGN PATENT DOCUMENTS

| | | |
|---|---|---|
| CN | 103384016 A | 11/2013 |
| CN | 105636970 A | 6/2016 |
| CN | 106661067 A | 5/2017 |
| JP | 2001-139584 A | 5/2001 |
| JP | 2001-516492 A | 9/2001 |
| JP | 2001-335590 A | 12/2001 |
| JP | 2005-190873 A | 7/2005 |
| JP | 2005-298491 A | 10/2005 |
| JP | 2006-131613 A | 5/2006 |
| JP | 2009-161559 A | 7/2009 |
| JP | 2009-235009 A | 10/2009 |
| JP | 2010-53086 A | 3/2010 |
| JP | 2012-171884 A | 9/2012 |
| JP | 2013-235830 A | 11/2013 |
| KR | 10-2013-0124180 A | 11/2013 |
| WO | WO 03/005479 A1 | 1/2003 |
| WO | WO 2007/114359 A1 | 10/2007 |
| WO | WO 2015/053302 A1 | 4/2015 |

OTHER PUBLICATIONS

Ito, JP2006131613 Machine Translation; 82 pages total.*
Chivers et al., Phosphonitrilic Derivatives. Part XIX. Dimethylaminofluorophosphonitriles and their Reactions with Hydrogen Halides as a Route to Monosubstituted and Non-geminal Derivatives of the Phosphonitrilic Fluorides, Journal of the Chemical Society (A): Inorganic, Physical, Theoretical, 1970, pp. 2324-2329.
International Search Report, issued in PCT/JP2015/068947, dated Sep. 29, 2015.
Written Opinion of the International Searching Authority, issued in PCT/JP2015/068947, dated Sep. 29, 2015.
English Translation of International Preliminary Report on Patentability (PCT/IB373 and PCT/ISA/237) for PCT/JP2015/068947, dated Jan. 10, 2017.
Korean Office Action dated Feb. 1, 2018 for corresponding Korean Application No. 10-2017-7001264, with a machine translation.
Chinese Office Action issued in Chinese Patent Application No. 201580034101.3 dated Feb. 24, 2018.
Evans et al:, "The Partial Aminolysis of (NPF2)3,4", Inorganic Chemistry, vol. 18, No. 9 (1979) pp. 2342-2344.

* cited by examiner

MANUFACTURING METHOD FOR AMINO-SUBSTITUTED PHOSPHAZENE COMPOUND, MANUFACTURING METHOD FOR ELECTROLYTE SOLUTION FOR NONAQUEOUS SECONDARY BATTERY, AND MANUFACTURING METHOD FOR NONAQUEOUS SECONDARY BATTERY

CROSS-REFERENCE TO RELATED APPLICATIONS

This application is a Continuation of PCT International Application No. PCT/JP2015/068947 filed on Jul. 1, 2015, which claims priority under 35 U.S.C. § 119 (a) to Japanese Patent Application No. JP2014-138947 filed on Jul. 4, 2014. Each of the above applications is hereby expressly incorporated by reference, in its entirety, into the present application.

BACKGROUND OF THE INVENTION

1. Field of the Invention

The present invention relates to a manufacturing method for an amino-substituted phosphazene compound, a manufacturing method for an electrolyte solution for a nonaqueous secondary battery using this, and a manufacturing method for a nonaqueous secondary battery.

2. Description of the Related Art

A phosphazene compound is applied to various uses. Particularly, a phosphazene compound is recently noticed as a compound that can provide excellent incombustibility to various materials. For example, a phosphazene compound is used as a compound that can provide incombustibility to a lithium ion secondary battery, to be an additive of an electrolyte solution thereof (see JP2005-190873A). In this document, a derivative obtained by substituting halogenated cyclic phosphazene with an alcohol compound is used as a flame retardant.

Recently, a synthesis method for a derivative obtained by introducing a specific substituent to a phosphazene compound is known. For example, with respect to the alkoxy-substituted fluorinated phosphazene, a method for reacting a compound represented by $(PNF_2)_n$ with alcoholate represented by R-OM (in the formula, R represents an alkyl group and M represents alkali metal) or alcohol represented by R-13 OH (in the formula, R has the same meaning as above) without a catalyst or in presence of a basic catalyst such as sodium carbonate and potassium carbonate is known (see JP2009-161559A, JP2001-335590A, JP2001-139584A, WO03/005479A, and JP2001-516492A).

With respect to the synthesis of fluorinated phosphazene in which an amino group is substituted, a method for reacting a compound represented by $(PNF_2)_n$ and two equivalents of amine (see Journal of the Chemical Society [Section] A: Inorganic, Physical, Theoretical, 1970, pages 2324 to 2329) is known. This document suggests performing amino substitution reaction by using dimethylaminotrimethylsilane.

SUMMARY OF THE INVENTION

With respect to the synthesis method for the phosphazene compound as described above, several methods has been suggested. However, the methods have not been sufficiently reviewed. Recently, as the phosphazene compound is widely used as a flame retardant applied to a battery, an electronic material, or the like, diversification of synthesis method is an indispensable object. Particularly, excellent incombustibility of an amino-substituted body is remarkable (see WO2013/047342A) and manufacturing techniques are required to be developed.

The invention is conceived in view of the above circumstances and an object thereof is providing a novel synthesis method of an amino-substituted phosphazene compound. If necessary, another object of the invention is providing a manufacturing method for manufacturing an amino-substituted phosphazene compound in high yield, high selectivity, and high purity and at an inexpensive cost and manufacturing methods for an electrolyte solution for a nonaqueous secondary battery and a nonaqueous secondary battery using this amino-substituted phosphazene compound.

Objects described above are achieved by means described below.

[1] A manufacturing method for an amino-substituted phosphazene compound comprising: reacting a fluorinated phosphazene compound and an amine compound in presence of a compound having a fluorine trapping function; and synthesizing a compound obtained by substituting the amine compound for the fluorinated phosphazene compound.

[2] The manufacturing method according to [1], in which the compound having a fluorine trapping function is a compound having a carbon-carbon unsaturated bond, a compound having a bond between silicon and oxygen, and fluoride of alkali metal or alkali earth metal.

[3] The manufacturing method according to [1] or [2], in which the compound having a fluorine trapping function is at least one selected from the group consisting of a compound represented by Formula (I-1) or (I-2) below, a compound represented by Formula (II-1) below, and a metal compound having a structure represented by Formula (III-1) below.

(I-1)

(I-2)

(II-1)

(III-1)

$R^{11}$ to $R^{14}$ each independently represent a hydrogen atom, an alkyl group, an alkenyl group, an alkynyl group, an aryl group, an aralkyl group, an alkoxy group, an aryloxy group, an aralkyloxy group, an amino group, a halogen atom, a carbonyl group-containing group, or a cyano group, and $R^{11}$ to $R^{14}$ that are adjacent to each other may form rings, $R^{15}$ and $R^{16}$ each independently represent an alkyl group, an alkenyl group, an alkynyl group, an aryl group, an aralkyl group, an alkoxy group, an aryloxy group, an aralkyloxy group, an amino group, a halogen atom, a carbonyl group-containing group, or a cyano group, and $R^{15}$ and $R^{16}$ that are adjacent to each other may form a ring, $R^{17}$ represents an alkyl group, an aryl group, or a carbonyl group-containing group, and $R^{18}$ to $R^{20}$ each independently represent a hydrogen atom, an alkyl group, an alkenyl group, an alkynyl group, an aryl group, an aralkyl group, an alkoxy group, an aryloxy group, an aralkyloxy group, an amino group, a halogen atom, or a carbonyl group-containing group, and M represents Li, Na, K, Cs, or Ca.

[4] The manufacturing method according to [3], in which the compound represented by Formula (I-1), (I-2), or (II-1) above is a compound having 2 to 16 carbon atoms.

[5] The manufacturing method according to any one of [1] to [4], in which the compound having a fluorine trapping function is added to the fluorinated phosphazene compound by 0.25 to 2 equivalents.

[6] The manufacturing method according to any one of [1] to [5], in which the amino-substituted phosphazene compound is a compound represented by Formula (1) below.

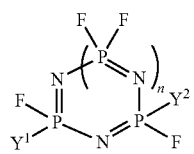

(1)

In the formula, $Y^1$ represents $-NR^1R^2$, $Y^2$ represents a fluorine atom or $-NR^3R^4$, $R^1$ to $R^4$ each independently represent a monovalent substituent or a hydrogen atom, $R^1$ and $R^2$ or $R^3$ and $R^4$ may form a ring, and n represents 1 or 2.

[7] The manufacturing method according to any one of claims [1] to [6], in which the fluorinated phosphazene compound is represented by Formula (2) below.

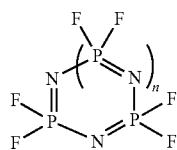

(2)

In the formula, n represents 1 or 2.

[8] The manufacturing method according to any one of [1] to [7], in which the number of carbon atoms of the amine compound is 1 to 12.

[9] A manufacturing method for an electrolyte solution for a nonaqueous secondary battery, comprising: preparing an electrolyte solution for a nonaqueous secondary battery containing the amino-substituted phosphazene compound via the manufacturing method according to any one of [1] to [8].

[10] A manufacturing method for a nonaqueous secondary battery, comprising: manufacturing a nonaqueous secondary battery including a cathode, an anode, and the electrolyte solution for a nonaqueous secondary battery by the manufacturing method according to [9].

In this specification, a numerical range represented by using an expression "to" is a range including numerical values described before and after the expression "to" as a lower limit and an upper limit.

According to the invention, it is possible to provide a novel synthesis method of an amino-substituted phosphazene compound. If necessary, it is possible to manufacture an amino-substituted phosphazene compound in high yield, high selectivity, and high purity and at an inexpensive cost. It is possible to provide manufacturing methods for an electrolyte solution for a nonaqueous secondary battery and a nonaqueous secondary battery using the amino-substituted phosphazene compound.

Characteristics described above, other characteristics, and advantages of the invention are appropriately exhibited below from descriptions below with reference to accompanying drawings.

DESCRIPTION OF THE PREFERRED EMBODIMENTS

Figure 1:
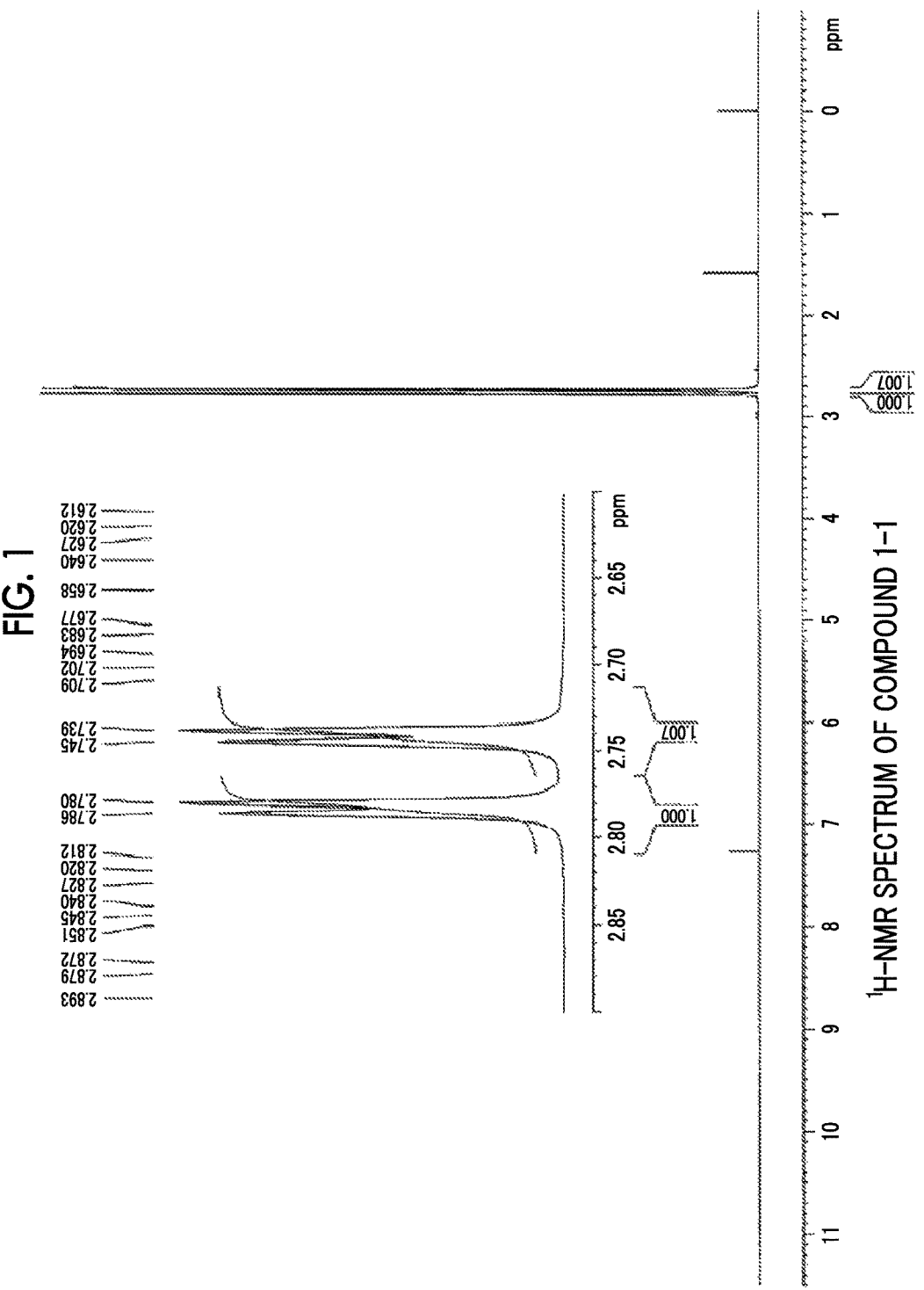
FIG. 1 is a $^1$H-NMR spectrum of a compound (1-1).

Hereinafter, the invention is described in detail. Descriptions of composition requirements described below are performed based on representative embodiments and specific examples. However, the invention is not limited to the embodiments.

In the manufacturing method according to the invention, an amino-substituted phosphazene compound is synthesized by reacting a fluorinated phosphazene compound and an amine compound in presence of a compound having a fluorine trapping function (hereinafter, referred to as a "fluorine trapping agent"). Hereinafter, the invention is described in detail mainly referring to preferable embodiments according to the invention.

<Amino-substituted Phosphazene Compound>

In the amino-substituted phosphazene compound synthesized in the invention, the number of substituted amino groups is not particularly limited, preferably 1 to 6, more preferably 1 to 4, and particularly preferably 1 or 2. According to the invention, the amino group has a meaning of including a substituted amino group (for example, an alkylamino group or an acylamino group). Preferable examples thereof include an amino group ($NR^1R^2$) (the same as $NR^3R^4$) identified in the substituent $Y^1$ below.

The phosphazene compound is preferably a cyclic phosphazene compound and more preferably a cyclic phosphazene compound of a 6-membered ring or an 8-membered ring.

The amino-substituted phosphazene compound is preferably a compound represented by Formula (1) below.

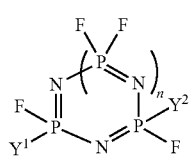

(1)

If groups other than $Y^1$ and $Y^2$ are fluorine atoms among halogen atoms, the groups contribute to providing particularly high incombustibility or maintaining battery performance, for example, when the groups are applied as additives (flame retardants) of a electrolyte solution of a lithium ion battery, and thus are preferable.

$Y^1$ represents —$NR^1R^2$. $R^1$ and $R^2$ each independently represent a monovalent substituent or a hydrogen atom and preferably represent a monovalent substituent. In $R^1$ and $R^2$, substituents may be form a ring with each other, or $R^1$ and $R^2$ may have an arbitrary substituent T. The substituent T is not particularly limited, and examples thereof include a halogen atom (for example, a fluorine atom), a carbonyl group-containing group (for example, a group having 2 to 6 carbon atoms), an alkoxy group (for example, an alkoxy group having 1 to 6 carbon atoms), and a silyl group (for example, a silyl group having 1 to 6 carbon atoms). Examples of the carbonyl group-containing group include groups defined by $R^{11}$ below.

$R^1$ and $R^2$ each independently and preferably represent a hydrogen atom, an alkyl group, and an alkenyl group. Among these, an alkyl group having 1 to 6 carbon atoms is preferable, an alkyl group having 1 to 4 carbon atoms is more preferable, and an alkyl group having 1 to 3 carbon atoms is particularly preferable. $R^1$ and $R^2$ are bonded or condensed to each other to form a ring. At this point, hetero atoms such as nitrogen atoms, oxygen atoms, and sulfur atoms may be integrated to each other. Specifically, a ring may be formed via a heterolinking group described below. As the formed ring, a 5-membered ring or a 6-membered ring is preferable. As the 5-membered ring, a nitrogen-containing 5-membered ring is preferable, and examples of compounds that form rings include pyrrole, imidazole, pyrazole, indazole, indole, benzimidazole, pyrrolidine, imidazolidine, pyrazolidine, indoline, and carbazole, and derivatives thereof (all are N-substituted). Examples of the 6-membered ring include piperidine, morpholine, and piperazine, and derivatives thereof (all are N-substituted).

$Y^2$ represents a fluorine atom or —$NR^3R^4$ and particularly preferably represents a fluorine atom. $R^3$ and $R^4$ are the same as $R^1$ and $R^2$, and preferable examples thereof are also the same as those of $R^1$ and $R^2$. $R^3$ and $R^4$ may form rings between substitutents thereof, and preferable examples thereof are also the same as those of $R^1$ and $R^2$. The reason that the fluorine atom is preferable among the halogen atoms is also the same as that described above. $R^3$ and $R^4$ each may have the arbitrary substituent T. Preferable examples of the substituent T are also the same as above.

n represents 1 or 2, and particularly preferably represents 1.

Formula (1) is described such that a cis-structure and a trans-structure are not differentiated and has a meaning of including the both. The same is also applied to interpretation of structural formulae of exemplified compounds below and a compound of Formula (2).

The preferable specific examples of the amino-substituted phosphazene compound are shown below. However, the invention is not limited by examples of compounds described below, at all.

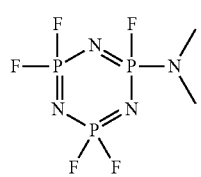

1-1

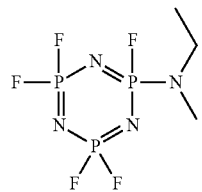

1-2

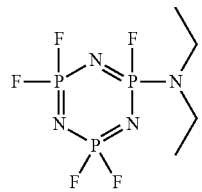

1-3

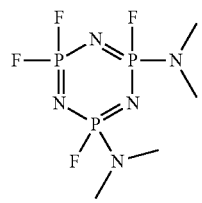

1-4

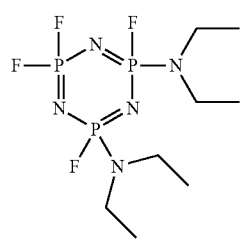

1-5

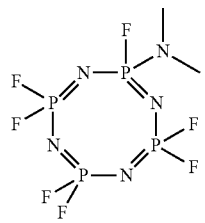

1-6

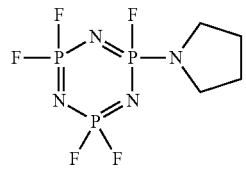

1-7

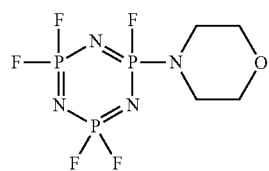

1-8

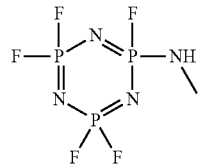

1-9

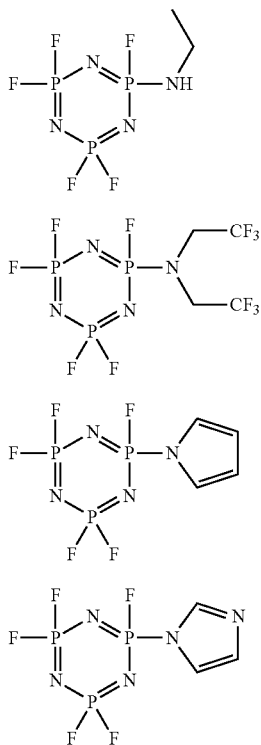

<Fluorinated Phosphazene Compound>

Subsequently, a compound represented by Formula (2) and an amine compound suitably used as a starting material compound used in a manufacturing method for the cyclic phosphazene derivative according to the invention are described.

The fluorinated phosphazene compound is preferably a compound represented by Formula (2) below.

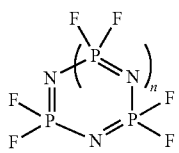

(2)

n represents 1 or 2 and particularly preferably represents 1.

According to the invention, as a reaction material, a fluorinated phosphazene compound is selected among the halogenated phosphazene compound. Reasons thereof include advantages on an application as described above, and also include advantages on reaction in a relationship with a compound having a fluorine trapping function (reaction assistant) employed in the invention. Halogenated phosphazene discharges a halogen atom in the system at the time of substitution reaction thereof. Among these, a fluorine anion has higher reactivity compared with a chlorine anion and the like (for example, see Chem. Ber. 116, 367-374, (1983) "Darstellung and Strukturbestimmung von Ammoniak-Phosphorpentafluorid (1/1)"). Therefore, a fluorine anion reacts with an unreacted base material, and generates a by-product, in some cases. In this case, a yield or selectivity of a desired compound decreases. In contrast, a compound having a fluorine trapping function suitably applied to the invention suppresses this side reaction and has an effect of increasing yield•selectivity. That is, it is construed that the compound has an effect of trapping a fluorine anion in a system. In view of notably exhibiting such effects, according to the invention, as described above, a base material having a fluorine atom as a halogen atom and a compound having a fluorine trapping function are used in combination.

According to the preferable embodiment of the invention, a monosubstituted product and a disubstituted product of an amino group (particularly, a monosubstituted product) can be selectively synthesized. The reason is not clear but it is construed that the compound having a fluorine trapping function is appropriate for a barrier in reaction due to the number of substitutions (respective steps of consecutive reaction) and selectively generates the number of substitutions of compounds. A monosubstituted product or a disubstituted product of an amino group of fluorinated phosphazene (particularly, a monosubstituted product) is particularly useful for a flame retardant (WO2013/047342A).

As a method for supplying fluorinated phosphazene compound, commercially available products may be used or fluorinated phosphazene compound may be appropriately synthesized in a usual method. As a synthesis method of the fluorinated phosphazene compound, for example, Schmutzler, R. Inorg. Synth. 1967, 9, 75 can be referred to.

<Amine Compound>

The amine compound refers to a compound having an amino group in a chemical structure and the amino group is preferably $NR^1R^2$ (also can be referred to as $NR^3R^4$) above. The amine compound preferably has 1 to 12 carbon atoms, more preferably has 1 to 8 carbon atoms, and particularly preferably has 1 to 6 carbon atoms. Though the number of carbon atoms is small, the number of carbon atoms is preferably 1 to 3. Specifically, the amine compound is preferably a compound represented by $H-NR^1R^2$, and examples thereof include methylamine, ethylamine, dimethylamine, diethylamine, and ethylmethylamine. Among these, dimethylamine and diethylamine are particularly preferable. $R^1$ and $R^2$ are the same as those defined in Formula (1) above. In the amine compound, as described above, $R^1$ and $R^2$ may form a ring, and preferable forms thereof are the same as those exemplified as rings formed by $R^1$ and $R^2$ of amino-substituted phosphazene.

In this reaction, hydrogen fluoride having an equivalent after substitution is generated. In order to neutralize the generated hydrogen fluoride, a basic compound may be added. Examples of the added basic compound include organic or inorganic compounds, but an organic salt group is particularly preferable. Examples of the organic salt group include triethylamine and diisopropylethylamine. In case of amine substitution reaction, amine used in the substitution may be used in neutralization. The compound having a fluorine trapping function is generally has a form in which fluorine in a system is integrated in this molecule when the reaction ends. Examples thereof include an example in which the compound of Formula (I-1) becomes a fluoroalkyl compound.

<Compound having Fluorine Trapping Function>

A compound having a fluorine trapping function in a synthesis reaction thereof is applied to the manufacturing method of the amino-substituted phosphazene compound according to the invention. The compound having this fluorine trapping function is preferably a compound having a carbon-carbon unsaturated bond (a double bond or a triple bond), a compound having a bond between silicon and oxygen, and fluoride of alkali metal or alkali earth metal.

The compound having a fluorine trapping function is preferably at least one selected from the group consisting of a compound represented by Formula (I-1) or (I-2) below, a compound represented by Formula (II-1) below, and a metal compound having a structure represented by Formula (III-1) below. The compound represented by Formula (I-1), (I-2), or (II-1) has preferably 2 to 16 carbon atoms, more preferably 3 to 10 carbon atoms, and particularly preferably 4 to 8 carbon atoms.

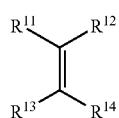

(I-1)

$R^{11}$ to $R^{12}$ each independently represent a hydrogen atom, an alkyl group (the number of carbon atoms is preferably 1 to 12, more preferably 1 to 6, and particularly preferably 1 to 3), an alkenyl group (the number of carbon atoms is preferably 2 to 12 and more preferably 2 to 6), an alkynyl group (the number of carbon atoms is preferably 2 to 12 and more preferably 2 to 6), an aryl group (the number of carbon atoms is preferably 6 to 22, more preferably 6 to 14, and particularly preferably 6 to 10), an aralkyl group (the number of carbon atoms is preferably 7 to 23, more preferably 7 to 15, and particularly preferably 7 to 11), an alkoxy group (the number of carbon atoms is preferably 1 to 12, more preferably 1 to 6, and particularly preferably 1 to 3), an aryloxy group (the number of carbon atoms is preferably 6 to 22, more preferably 6 to 14, and particularly preferably 6 to 10), an aralkyloxy group (the number of carbon atoms is preferably 7 to 23, more preferably 7 to 15, and particularly preferably 7 to 11), an amino group (the number of carbon atoms is preferably 0 to 12, more preferably 0 to 6, and particularly preferably 0 to 3), a halogen atom (for example, a fluorine atom), a carbonyl group-containing group (the number of carbon atoms is preferably 2 to 12, and more preferably 2 to 6), or a cyano group. Among these, an alkyl group, an aryl group, an alkoxy group, a halogen atom, a carbonyl group-containing group, or a cyano group is preferable, an alkyl group, an aryl group, an alkoxy group, a carbonyl group-containing group, or a cyano group is more preferable, and an alkyl group or an aryl group is particularly preferable.

Examples of the carbonyl group-containing group include an acyl group (the number of carbon atoms is preferably 2 to 12 and more preferably 2 to 6, an acetyl group, a propionyl group, and the like), an alkoxycarbonyl group (the number of carbon atoms is preferably 2 to 12 and more preferably 2 to 6, a methoxycarbonyl group, an isopropoxycarbonyl group, and the like), an aryloxycarbonyl group (the number of carbon atoms is preferably 7 to 23, more preferably 7 to 15, and particularly preferably 7 to 10), an aralkyloxycarbonyl group (the number of carbon atoms is preferably 8 to 24, more preferably 8 to 16, and particularly preferably 8 to 11), an aryloyl group (the number of carbon atoms is preferably 7 to 23, more preferably 7 to 15, and particularly preferably 7 to 10, a benzoyl group or the like), an acyloxy group (the number of carbon atoms is preferably 2 to 12 and more preferably 2 to 6, an acetyloxy group, a propionyloxy group, and the like), an aryloyloxy group (the number of carbon atoms is preferably 7 to 23, more preferably 7 to 15, and particularly preferably 7 to 10, a benzoyloxy group, and the like), a (meth)acryloyl group, a (meth)acryloyloxy group, and a carbamoyl group (the number of carbon atoms is preferably 1 to 12, more preferably 1 to 6, and particularly preferably 1 to 3, a carbamoyl group, an N-methylcarbamoyl group, an N,N-dimethylcarbamoyl group, an N-phenylcarbamoyl group, and the like).

$R^{11}$ to $R^{14}$ that are adjacent to each other may form rings. The formed rings are preferably 4-membered to 6-membered rings, and more preferably an alicyclic structure of 4-membered to 6-membered rings. The number of atoms that form a ring is preferably 3 to 12 and more preferably 4 to 6. When a ring is formed, a hetero linking group described below may be integrated or a portion thereof may be condensed. Specific examples thereof include cycloalkene, and cyclopropene, cyclobutene, cyclopentene, cyclohexene, cycloheptene, cyclooctene, norbornene, and norbornadiene are preferable.

Examples of the compound corresponding to Formula (I-1) includes below. However, the invention is not limited thereto.

(I-1a)

(I-1b)

(I-1c)

(I-1d)

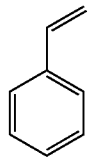

(I-1e)

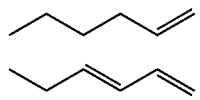

(I-1f)

(I-1g)

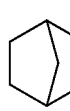

(I-1h)

(I-1i)

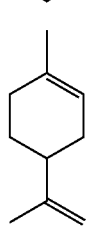

(I-1j)

-continued

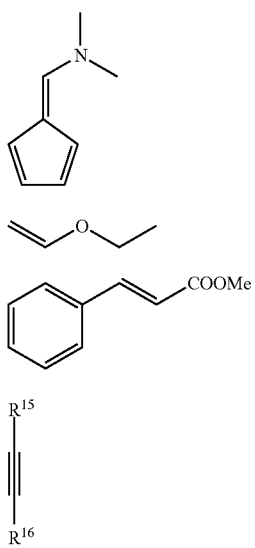

(I-1k)

(I-1l)

(I-1m)

(I-2)

Examples of the compound corresponding to Formula (I-2) includes below. However, the invention is not limited thereto.

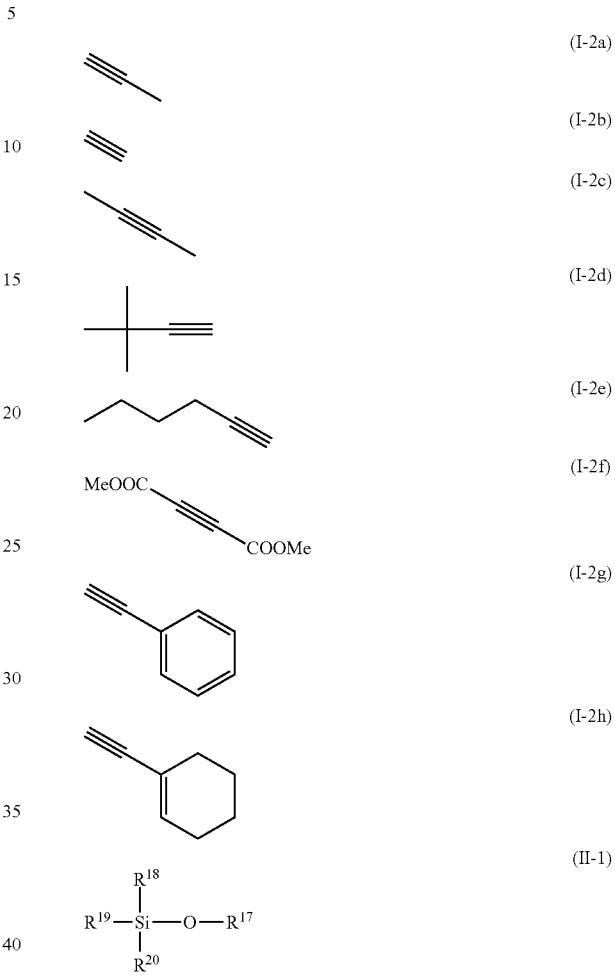

$R^{15}$ and $R^{16}$ each independently represent a hydrogen atom, an alkyl group (the number of carbon atoms is preferably 1 to 12, more preferably 1 to 6, and particularly preferably 1 to 3), an alkenyl group (the number of carbon atoms is preferably 2 to 12 and more preferably 2 to 6), an alkynyl group (the number of carbon atoms is preferably 2 to 12 and more preferably 2 to 6), an aryl group (the number of carbon atoms is preferably 6 to 22, more preferably 6 to 14, and particularly preferably 6 to 10), an aralkyl group (the number of carbon atoms is preferably 7 to 23, more preferably 7 to 15, and particularly preferably 7 to 11), an alkoxy group (the number of carbon atoms is preferably 1 to 12, more preferably 1 to 6, and particularly preferably 1 to 3), an aryloxy group (the number of carbon atoms is preferably 6 to 22, more preferably 6 to 14, and particularly preferably 6 to 10), an aralkyloxy group (the number of carbon atoms is preferably 7 to 23, more preferably 7 to 15, and particularly preferably 7 to 11), an amino group (the number of carbon atoms is preferably 0 to 12, more preferably 0 to 6, and particularly preferably 0 to 3), a halogen atom (for example, a fluorine atom), a carbonyl group-containing group (the number of carbon atoms is preferably 2 to 12, and more preferably 2 to 6), or a cyano group. Among these, an alkyl group, an aryl group, an alkoxy group, a halogen atom, a carbonyl group-containing group, or a cyano group is preferable, an alkyl group, an aryl group, an alkoxy group, a carbonyl group-containing group, or a cyano group is more preferable, and an alkyl group, an aryl group, or a carbonyl group-containing group is particularly preferable. As a carbonyl group-containing group, a group the same as $R^{11}$ is preferable. In this specification, an alkyl group, an alkenyl group, and an alkynyl group may have a cyclic structure. However, with respect to the compound in this formula, in a case of an alkenyl group, a preferable form thereof include a cycloalkenyl group (the number of carbon atoms is preferably 3 to 12 and more preferably 3 to 6).

$R^{15}$ and $R^{16}$ may form a ring. The formed rings are preferably 4-membered to 6-membered rings, and more preferably an alicyclic structure of 4-membered to 6-membered rings. The number of atoms that form a ring is preferably 3 to 12 and more preferably 4 to 6. When a ring is formed, a hetero linking group described below may be integrated or a portion thereof may be condensed.

$R^{17}$ represent an alkyl group (the number of carbon atoms is preferably 1 to 12, more preferably 1 to 6, and particularly preferably 1 to 3), an aryl group (the number of carbon atoms is preferably 6 to 22, more preferably 6 to 14, and particularly preferably 6 to 10), or a carbonyl group-containing group (the number of carbon atoms is preferably 2 to 12, and more preferably 2 to 6). Preferable examples of a carbonyl group-containing group include a group the same as $R^{11}$. Examples of a carbonyl group-containing group include an acyl group (the number of carbon atoms is preferably 2 to 12 and more preferably 2 to 6, an acetyl group, a propionyl group, and the like), an alkoxycarbonyl group (the number of carbon atoms is preferably 2 to 12 and more preferably 2 to 6, a methoxycarbonyl group, an isopropoxycarbonyl group, and the like), an aryloxycarbonyl group (the number of carbon atoms is preferably 7 to 23, more preferably 7 to 15, and particularly preferably 7 to 10), an aralkyloxycarbonyl group (the number of carbon atoms is preferably 8 to 24, more preferably 8 to 16, and particularly preferably 8 to 11), an aryloyl group (the number of carbon atoms is preferably 7 to 23, more preferably 7 to 15, and particularly preferably 7 to 11, a benzoyl group, and the like), a (meth)acryloyl group, a carbamoyl group (the number of carbon atoms is preferably 1 to 12, more preferably 1 to 6, and particularly preferably 1 to 3, a carbamoyl group, a N-methylcarbamoyl group, a N,N-dimethylcarbamoyl group, a N-phenylcarbamoyl group, and the like). Among these, an alkyl group and an aryl group are preferable.

$R^{18}$ to $R^{20}$ each independently represent a hydrogen atom, an alkyl group (the number of carbon atoms is preferably 1 to 12, more preferably 1 to 6, even more preferably 1 to 3, and particularly preferably 1 or 2), an alkenyl group (the number of carbon atoms is preferably 2 to 12 and more preferably 2 to 6), an alkynyl group (the number of carbon atoms is preferably 2 to 12 and more preferably 2 to 6), an aryl group (the number of carbon atoms is preferably 6 to 22, more preferably 6 to 14, and particularly preferably 6 to 10), an aralkyl group (the number of carbon atoms is preferably 7 to 23, more preferably 7 to 15, and particularly preferably 7 to 11), an alkoxy group (the number of carbon atoms is preferably 1 to 12, more preferably 1 to 6, and particularly preferably 1 to 3), an aryloxy group (the number of carbon atoms is preferably 6 to 22, more preferably 6 to 14, and particularly preferably 6 to 10), an aralkyloxy group (the number of carbon atoms is preferably 7 to 23, more preferably 7 to 15, and particularly preferably 7 to 11), an amino group (the number of carbon atoms is preferably 0 to 12, more preferably 0 to 6, and particularly preferably 0 to 3), or a halogen atom (for example, a fluorine atom), a carbonyl group-containing group (the number of carbon atoms is preferably 2 to 12, and more preferably 2 to 6). Among these, an alkyl group, an alkenyl group, an aryl group, an alkoxy group, a halogen atom, or a carbonyl group-containing group is preferable, an alkyl group, an alkenyl group, an aryl group, or an alkoxy group is more preferable, and an alkyl group, an aryl group, or an alkoxy group is particularly preferable. As a carbonyl group-containing group, a group the same as $R^{11}$ is preferable.

$R^{17}$ to $R^{20}$ that are adjacent to each other may form rings. The formed rings are preferably 4-membered to 6-membered rings, and more preferably an alicyclic structure of 4-membered to 6-membered rings. The number of atoms that form a ring is preferably 3 to 12 and more preferably 4 to 6.

Examples of the compound corresponding to Formula (II-1) includes below. However, the invention is not limited thereto.

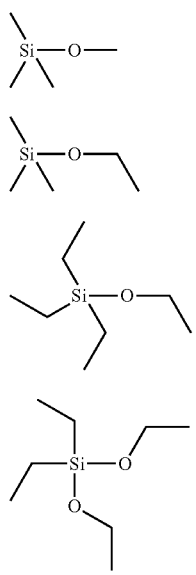

(II-1a)

(II-1b)

(II-1c)

(II-1d)

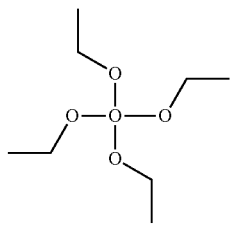

(II-1e)

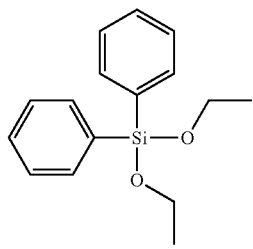

(II-1f)

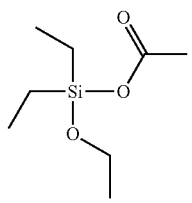

(II-1g)

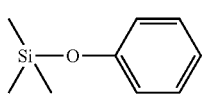

(II-1h)

M—F  (III-1)

M represents Li, Na, K, Cs, or Ca. A compound having a structure of Formula (III-1) is preferably a compound represented by MFn. n is a number of greater than 0, is preferably a number of greater than 0 and equal to or smaller than 6, and more preferably 1 or 2. Examples of a metal compound having a structure represented by Formula (III-1) include potassium fluoride, sodium fluoride, lithium fluoride, cesium fluoride, and calcium fluoride.

According to the invention, a compound having a fluorine trapping function may be used singly or two or more types thereof may be used in combination.

In view of cost, the use amount of the compound having a fluorine trapping function is preferably 0.01 equivalents or greater, more preferably 0.05 equivalents or greater, even more preferably 0.2 equivalents or greater, and particularly preferably 0.25 equivalents or greater with respect to the fluorinated phosphazene compound that is a starting raw material. The upper limit thereof is preferably 5 equivalents or less, more preferably 3 equivalents or less, even more preferably 2 equivalents or less, and particularly preferably 1 equivalent or less.

In view of manufacturing efficiency, the temperature of this reaction is preferably −20° C. or higher, more preferably −15° C. or higher, and particularly preferably −10° C. or higher. The upper limit thereof is preferably 100° C. or lower, more preferably 60° C. or lower, and particularly preferably 50° C. or lower. The time of this reaction is preferably within 24 hours, more preferably within 10 hours, even more preferably within 5 hours, and particularly preferably within 3 hours. After the reaction ends, purification such as liquid separation and distillation can be performed, if necessary.

In this specification, a description of a compound (in a case of adding the expression "compound" at an end) is used as a meaning of including salts thereof, and ions thereof, in addition to the compound itself. The description has a meaning of including derivatives in which a part is changed, for example, a substituent is introduced, in the scope of exhibiting a desired effect.

In this specification, with respect to a substituent (the same is applied to a linking group) in which substitution•non-substitution is not described, the substituent has a meaning that may have an arbitrary substituent in the group. The same can be also applied to a compound in which substitution•non-substitution is not described. Preferable examples of the substituent include a substituent Z below.

Examples of the substituent Z include the followings.

Examples are an alkyl group (preferably an alkyl group having 1 to 20 carbon atoms, for example, methyl, ethyl, isopropyl, t-butyl, pentyl, heptyl, 1-ethylpentyl, benzyl, 2-ethoxyethyl, and 1-carboxymethyl), an alkenyl group (preferably an alkenyl group having 2 to 20 carbon atoms, for example, vinyl, allyl, and oleyl), an alkynyl group (preferably an alkynyl group having 2 to 20 carbon atoms, for example, ethynyl, butadiynyl, and phenylethynyl), a cycloalkyl group (preferably a cycloalkyl group having 3 to 20 carbon atoms, for example, cyclopropyl, cyclopentyl, cyclohexyl, and 4-methylcyclohexyl), an aryl group (preferably an aryl group having 6 to 26 carbon atoms, for example, phenyl, 1-naphthyl, 4-methoxyphenyl, 2-chlorophenyl, and 3-methylphenyl), a heterocyclic group (preferably a heterocyclic group having 2 to 20 carbon atoms, and more preferably a heterocyclic group of a 5 or 6-membered ring having at least one of an oxygen atom, a sulfur atom, or a nitrogen atom, and examples thereof include 2-pyridyl, 4-pyridyl, 2-imidazolyl, 2-benzimidazolyl, 2-thiazolyl, and 2-oxazolyl), an alkoxy group (preferably an alkoxy group having 1 to 20 carbon atoms, for example, methoxy, ethoxy, isopropyloxy, and benzyloxy), an aryloxy group (preferably an aryloxy group having 6 to 26 carbon atoms, for example, phenoxy, 1-naphthyloxy, 3-methylphenoxy, and 4-methoxyphenoxy), an alkoxycarbonyl group (preferably an alkoxycarbonyl group having 2 to 20 carbon atoms, for example, ethoxycarbonyl and 2-ethylhexyloxycarbonyl), an aryloxycarbonyl group (preferably an aryl oxycarbonyl group having 6 to 26 carbon atoms, for example, phenoxycarbonyl, 1-naphthyloxycarbonyl, 3-methylphenoxycarbonyl, and 4-methoxy phenoxycarbonyl), an amino group (preferable examples thereof include an amino group having 0 to 20 carbon atoms, an alkylamino group, and an arylamino group, and, for example, amino, N,N-dimethylamino, N,N-diethylamino, N-ethylamino, and anilino), a sulfamoyl group (preferably a sulfamoyl group having 0 to 20 carbon atoms, for example, N,N-dimethylsulfamoyl and N-phenylsulfamoyl), an acyl group (preferably an acyl group having 1 to 20 carbon atoms, for example, acetyl, propionyl, and butyryl), an aryloyl group (preferably an aryloyl group having 7 to 23 carbon atoms, for example, benzoyl), an acyloxy group (preferably an acyloxy group having 1 to 20 carbon atoms, for example, an acetyloxy group), an aryloyloxy group (preferably an aryloyloxy group having 7 to 23 carbon atoms, for example, benzoyloxy), a carbamoyl group (preferably a carbamoyl group having 1 to 20 carbon atoms, for example, N,N-dimethylcarbamoyl and N-phenylcarbamoyl), an acylamino group (preferably an acylamino group having 1 to 20 carbon atoms, for example, acetylamino and benzoylamino), an alkylthio group (preferably an alkylthio group having 1 to 20 carbon atoms, for example, methylthio, ethylthio, isopropylthio, and benzylthio), an arylthio group (preferably an arylthio group having 6 to 26 carbon atoms, for example, phenylthio, 1-naphthylthio, 3-methylphenylthio, and 4-methoxyphenylthio), an alkylsulfonyl group (preferably an alkylsulfonyl group having 1 to 20 carbon atoms, for example, methylsulfonyl and ethylsulfonyl), an arylsulfonyl group (preferably an arylsulfonyl group having 6 to 22 carbon atoms, for example, benzenesulfonyl), a silyl group (preferably a silyl group having 1 to 20 carbon atoms, for example, monomethylsilyl, dimethylsilyl, trimethylsilyl, triethylsilyl, and triphenylsilyl), a phosphoryl group (preferably a phosphoryl group having 0 to 20 carbon atoms, for example, —OP(=O)($R^P$)$_2$), a phosphonyl group (preferably a phosphonyl group having 0 to 20 carbon atoms, for example, —P(=O)($R^P$)$_2$), a phosphinyl group (preferably a phosphinyl group having 0 to 20 carbon atoms, for example, —P($R^P$)$_2$), a (meth)acryloyl group, a (meth)acryloyloxy group, a hydroxyl group, a cyano group, and a halogen atom (for example, a fluorine atom, a chlorine atom, a bromine atom, and an iodine atom).

These respective groups provided as the substituent Z may be further substituted with the substituent Z above.

When a compound, a substituent•linking group, or the like includes an alkyl group•an alkylene group, an alkenyl group•an alkenylene group, an alkynyl group•an alkynylene group, and the like, these may have a cyclic form or a chain form, may have a straight chain form or a branched form, and may be or may not be substituted. When an aryl group, a heterocyclic group, or the like is included, these may be single rings or condensed rings, and may be or may not be substituted, in the same manner.

In the range that exhibits the effect of the invention, the respective substituents defined in this specification may be substituted with the linking group L below interposed therebetween. For example, an alkyl group•an alkylene group, an alkenyl group•an alkenylene group, and the like may further have a following hetero linking group interposed therebetween in the structure.

As the linking group L, a hydrocarbon linking group [an alkylene group having 1 to 10 carbon atoms (the number of carbon atoms is more preferably 1 to 6 and further preferably 1 to 3), an alkenylene group having 2 to 10 carbon atoms (the number of carbon atoms is more preferably 2 to 6 and even more preferably 2 to 4), an arylene group having 6 to 22 carbon atoms (the number of carbon atoms is more preferably 6 to 10)], a hetero linking group [a carbonyl group (—CO—), an ether group (—O—), a thioether group (—S—), an imino group (—$NR^N$—), an imine linking group ($R^N$—N=C< and —N=C($R^N$)—)], or a linking group obtained by combining these is preferable. In addition, if a condensed ring is formed, the hydrocarbon linking group may be linked to appropriately form a double bond or a triple bond.

$R^N$ is a hydrogen atom or a substituent. As the substituent, an alkyl group (the number of carbon atoms is preferably 1 to 24, more preferably 1 to 12, even more preferably 1 to 6, and particularly preferably 1 to 3), an alkenyl group (the number of carbon atoms is preferably 2 to 24, more preferably 2 to 12, even more preferably 2 to 6, and particularly preferably 2 or 3), an alkynyl group (the number of carbon atoms is preferably 2 to 24, more preferably 2 to 12, even more preferably 2 to 6, and particularly preferably 2 or 3), an aralkyl group (the number of carbon atoms is preferably 7 to 22, more preferably 7 to 14, and particularly preferably 7 to 10), and an aryl group (the number of carbon atoms is preferably 6 to 22, more preferably 6 to 14, and particularly preferably 6 to 10) are preferable.

$R^P$ represents a hydrogen atom, a hydroxyl group, or a substituent. As the substituent, an alkyl group (the number of carbon atoms is preferably 1 to 24, more preferably 1 to 12, even more preferably 1 to 6, and particularly preferably 1 to 3), an alkenyl group (the number of carbon atoms is preferably 2 to 24, more preferably 2 to 12, even more preferably 2 to 6, and particularly preferably 2 or 3), an alkynyl group (the number of carbon atoms is preferably 2 to 24 carbon atoms, more preferably 2 to 12, even more preferably 2 to 6, and particularly preferably 2 or 3), an aralkyl group (the number of carbon atoms is preferably 7 to 22, more preferably 7 to 14, and particularly preferably 7 to 10), an aryl group (the number of carbon atoms is preferably 6 to 22, more preferably 6 to 14, and particularly preferably 6 to 10), an alkoxy group (the number of carbon atoms is preferably 1 to 24, more preferably 1 to 12, even more preferably 1 to 6, and particularly preferably 1 to 3), an alkenyloxy group (the number of carbon atoms is preferably 2 to 24, more preferably 2 to 12, even more preferably 2 to 6, and particularly preferably 2 or 3), an alkynyloxy group (the number of carbon atoms is preferably 2 to 24, more preferably 2 to 12, even more preferably 2 to 6, and particularly preferably 2 or 3), an aralkyloxy group (the number of carbon atoms is preferably 7 to 22, more preferably 7 to 14, and particularly preferably 7 to 10), and an aryloxy group (the number of carbon atoms is preferably 6 to 22, more preferably 6 to 14, and particularly preferably 6 to 10) are preferable.

In this specification, the number of atoms that form a linking group is preferably 1 to 36, more preferably 1 to 24, further preferably 1 to 12, and particularly preferably 1 to 6. The number of linking atoms in the linking group is preferably 10 or less and more preferably 8 or less. The lower limit is 1 or greater. The number of linking atoms above refers to a minimum number of atoms that are positioned in a path that connects certain structural portions and participate in the connection. For example, in the case of —CH$_2$—C(=O)—O—, the number of atoms that configure a linking group is 6, but the number of linking atoms is 3.

In the specification, when there are plural substituents or linking groups represented by specific reference symbols, or plural substituents and the like (the number of substituents is also defined in the same manner) are simultaneously or alternatively defined, respective substituents and the like may be identical to or different from each other. If the plural substituents and linking groups come close to each other, the substituents and the linking groups may form a ring by being bonded to each other or being condensed.

<Reaction Solvent>

In the manufacturing method according to the invention, a reaction solvent may not be used, but it is preferable to perform the manufacturing method by using the reaction solvent. Examples of the organic solvent include an aliphatic hydrocarbon compound, a halogenated hydrocarbon compound, an ether compound, an ester compound, a ketone compound, a nitrile compound, an amide compound, a sulfoxide compound, a carboxylic acid compound, an aromatic hydrocarbon compound, and a urea compound.

Examples of the aliphatic hydrocarbon compound include pentane, hexane, or cyclohexane.

Examples of the halogenated hydrocarbon compound include methylene chloride, chloroform, or 1,2-dichloroethane.

Examples of the ether compound include diethyl ether, diisopropyl ether, tertiary butyl methyl ether, dioxane, tetrahydrofuran, anisole, ethylene glycol dimethyl ether, diethylene glycol dimethyl ether, or diethylene glycol diethyl ether.

Examples of the ester compound include methyl acetate, ethyl acetate, propyl acetate, isopropyl acetate, or butyl acetate.

Examples of the ketone compound include acetone, 2-butanone, or 4-methyl-2-pentanone.

Examples of the nitrile compound include acetonitrile.

Examples of the amide compound include N,N-dimethylformamide, N,N-dimethylacetamide, or N-methylpyrrolidone.

Examples of the sulfoxide compound include dimethyl sulfoxide or sulfolane.

Examples of the aromatic hydrocarbon compound include benzene, chlorobenzene, dichlorobenzene, nitrobenzene, toluene, or xylene.

Examples of the urea compound include 1,3-dimethyl-2-imidazolidinone.

As the reaction solvent, a non-polar solvent and a polar solvent can be used. The non-polar solvent is not particularly limited, as long as the non-polar solvent is a solvent of which a dipole moment of a molecule that forms a solvent is 0 or a low value. Examples thereof include hexane, pentane, cyclohexane, and toluene. Among these, in view of good handleability and a low cost, hexane is particularly preferable.

The polar solvent described above is not particularly limited, as long as the polar solvent is a solvent in which molecules that form the solvent have dipole moments. Examples thereof include acetonitrile, tetrahydrofuran, diethyl ether, tertiary butyl methyl ether, ethyl acetate, acetone, nitrobenzene, dimethylacetamide, and N-methylpyrrolidone. In view of good handleability, acetonitrile, tertiary butyl methyl ether, and tetrahydrofuran are preferable, and acetonitrile is particularly preferable. The reaction solvent may be used singly, two or more types thereof may be used in combination, and reaction may be performed in a two-phase system.

The amino-substituted phosphazene compound obtained in the manufacturing method according to the invention can be used in various uses. For example, the amino-substituted phosphazene compound can be applied as a flame retardant such as a resin, an electrolyte solution, a lubricant, and paint that is applied to various electrical devices and industrial products. Otherwise, the amino-substituted phosphazene compound can be used as insecticide (see DE2139691A). Recently, as the use that is highly demanded, the use in a nonaqueous secondary battery is exemplified. Hereinafter, an outline of a preferable embodiment at the time of being applied to a nonaqueous secondary battery is described.

<Electrolyte Solution for Nonaqueous Secondary Battery>

(Electrolyte)

An electrolyte solution for a nonaqueous secondary battery is applied to the nonaqueous secondary battery according to this embodiment. It is preferable that the electrolyte used in the electrolyte solution is a salt of a metal ion belonging to Groups I and II in the periodic table. The materials thereof are appropriately selected depending on the usage purposes of the electrolyte solution. Examples thereof include a lithium salt, a potassium salt, a sodium salt, a calcium salt, and a magnesium salt, and in view of an output, a lithium salt is preferable. In a case where the materials are used in a secondary battery, in view of an output, a lithium salt is preferable. In a case where an amino-substituted phosphazene compound manufactured in the manufacturing method according to the invention is used as a nonaqueous electrolyte solution for a lithium secondary battery, it is preferable to select lithium salt as salt of a metal ion. As the lithium salt, lithium salt that is generally used in an electrolyte of a nonaqueous electrolyte solution for a lithium secondary battery is preferable and is not particularly limited. For example, lithium salt described below is preferable.

(L-1) Inorganic lithium salt: Inorganic fluoride salt such as $LiPF_6$, $LiBF_4$, $LiAsF_6$, and $LiSbF_6$; perhalogen acid salt such as $LiClO_4$, $LiBrO_4$, and $LiIO_4$; and inorganic chloride salt such as $LiAlCl_4$.

(L-2) Fluorine-containing organic lithium salt: Perfluoroalkanesulfonic acid salt such as $LiCF_3SO_3$; perfluoroalkanesulfonyl imide salt such as $LiN(CF_3SO_2)_2$, $LiN(CF_3CF_2SO_2)_2$, $LiN(FSO_2)_2$, and $LiN(CF_3SO_2)(C_4F_9SO_2)$; perfluoroalkanesulfonyl methide salt such as $LiC(CF_3SO_2)_3$; and fluoroalkyl fluorophosphate such as $Li[PF_5(CF_2CF_2CF_3)]$, $Li[PF_4(CF_2CF_2CF_3)_2]$, $Li[PF_3(CF_2CF_2CF_3)_3]$, $Li[PF_5(CF_2CF_2CF_2CF_3)]$, $Li[PF_4(CF_2CF_2CF_2CF_3)_2]$, and $Li[PF_3(CF_2CF_2CF_2CF_3)_3]$.

(L-3) Oxalatoborate salt: Lithium bis(oxalato)borate and lithium difluorooxalatoborate.

Among these, $LiPF_6$, $LiBF_4$, $LiAsF_6$, $LiSbF_6$, $LiClO_4$, $Li(Rf^1SO_3)$, $LiN(Rf^1SO_2)_2$, $LiN(FSO_2)_2$, and $LiN(Rf^1SO_2)(Rf^2SO_2)$ are preferable, and lithium salt such as $LiPF_6$, $LiBF_4$, $LiN(Rf^1SO_2)_2$, $LiN(FSO_2)_2$, and $LiN(Rf^1SO_2)(Rf^2SO_2)$ is more preferable. Here, $Rf^1$ and $Rf^2$ each represent a perfluoroalkyl group.

The electrolytes used in the electrolyte solution may be used singly, or two or more types thereof may be arbitrarily combined.

It is preferable that the electrolyte (preferably an ion of a metal belonging to Groups I and II in the periodic table or metal salt thereof) in the electrolyte solution is added in an amount for a preferable salt concentration described below in a preparation method for an electrolyte solution. The salt concentration is appropriately selected depending on the usage purpose of the electrolyte solution, but is generally 10% by mass to 50% by mass with respect to the total mass of the electrolyte solution and more preferably 15% by mass to 30% by mass. As a molar concentration, 0.5 M to 1.5 M is preferable. In addition, when the evaluation is performed with a concentration of an ion, the concentration may be estimated in terms of a salt with metal preferably applied.

(Nonaqueous Solvent)

As the nonaqueous solvent that is used in the electrolyte solution according to this embodiment, an aprotic organic solvent is preferable. Among aprotic organic solvents, an aprotic organic solvent having 2 to 10 carbon atoms is preferable. The nonaqueous solvent is preferably formed with a compound having an ether group, a carbonyl group, an ester group, or a carbonate group. The compound may have a substituent.

Examples of nonaqueous solvent include ethylene carbonate, propylene carbonate, butylene carbonate, dimethyl carbonate, diethyl carbonate, ethyl methyl carbonate, methyl propyl carbonate, γ-butyrolactone, γ-valerolactone, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, methyl acetate, ethyl acetate, methyl propionate, ethyl propionate, methyl butyrate, methyl isobutyrate, methyl trimethyl acetate, ethyl trimethyl acetate, acetonitrile, glutaronitrile, adiponitrile, methoxyacetonitrile, 3-methoxypropionitrile, N,N-dimethylformamide, N-methylpyrrolidinone, N-methyloxazolidinone, N,N'-dimethylimidazolidinone, nitromethane, nitroethane, sulfolane, trimethyl phosphate, dimethyl sulfoxide, or dimethyl sulfoxide phosphate. These may be used singly or two or more types thereof may be used in combination. Among these, at least one selected from the group consisting of ethylene carbonate, propylene carbonate, dimethyl carbonate, diethyl carbonate, ethyl methyl carbonate, and γ-butyrolactone is preferable. Particularly, a combination of a solvent having high viscosity (high dielectric constant) (for example, relative dielectric constant ∈≥30) such as ethylene carbonate or propylene carbonate and a solvent having low viscosity (for example, viscosity ≤1 mPa·s) such as dimethyl carbonate, ethyl methyl carbonate, or diethyl carbonate is more preferable. This is because dissociation of electrolyte salt and mobility of ions increase.

However, the nonaqueous solvent used in the invention is not limited to the examples above.

(Method for Preparing Electrolyte Solution)

The manufacturing method for an electrolyte solution for a nonaqueous secondary battery according to the invention can be performed by performing the manufacturing method of the amino-substituted phosphazene compound and preparing an electrolyte solution for a nonaqueous secondary battery containing the amino-substituted phosphazene compound. Specific examples thereof include an example in which lithium salt is used as salt of metal ions. Respective components thereof are prepared in a usual method by dissolving the nonaqueous electrolyte solution solvent.

<Nonaqueous Secondary Battery>

The manufacturing method for a nonaqueous secondary battery according to the invention can be performed by performing the manufacturing method of the electrolyte solution for a nonaqueous secondary battery and manufacturing a battery including a cathode, an anode, and the electrolyte solution for a nonaqueous secondary battery.

The lithium ion secondary battery according to a preferable embodiment of the invention includes an electrolyte solution for the nonaqueous secondary battery according to the invention, a cathode (a cathode collector and a cathode active material layer) that can insert and discharge lithium ions, and an anode (an anode collector and an anode active material layer) that can insert and discharge or dissolve and deposit lithium ions. In addition to these essential members, in consideration of the purpose of using the battery, the form of the potentials, and the like, the nonaqueous secondary battery may be configured to include a separator that is arranged between the cathode and the anode, a collecting terminal, an exterior case, and the like. If necessary, a protection element may be mounted on at least one of an internal portion of the battery or an outer portion of the battery. With this structure, transfer of lithium ions in the electrolyte solution occurs, charging and discharging are performed, and driving or condensation may be performed via circuit wiring and operation mechanism. Hereinafter, respective members are described.

(Electrode Composite Material)

The electrode composite material is formed by applying a dispersoid such as an active material, a conductive agent, a binding agent, a filler, and the like to a collector (electrode substrate). In the lithium battery, it is preferable that a cathode mixture of which an active material is a cathode active material and an anode mixture of which an active material is an anode active material are used. Subsequently, respective components in a dispersoid (composition for electrode) that configures the electrode composite material are described.

Cathode Active Material

It is preferable that a lithium-containing transition metal oxide is used in the cathode active material. Among these, it is preferable that a transition element $M^a$ (one or more elements selected from Co, Ni, Fe, Mn, Cu, and V) is included. In addition, a mixture element $M^b$ (an element in Group 1 (Ia) in the periodic table of metals other than lithium, an element in Group 2 (IIa), Al, Ga, In, Ge, Sn, Pb, Sb, Bi, Si, P, B, and the like) may be mixed. Examples of this lithium-containing transition metal oxide include specific transition metal oxides including those represented by any one of Formulae (MA) to (MC) below, or $V_2O_5$, $MnO_2$, and the like as other transition metal oxide. A particle-shaped cathode active material may be used as the cathode active material. Specifically, it is possible to use a transition metal oxide that can reversibly insert•discharge lithium ions, but it is preferable to use the specific transition metal oxides described above.

As the lithium-containing transition metal oxide, an oxide including the transition element $M^a$ is suitably included. At this point, a mixture element $M^b$ (preferably Al) and the like may be mixed. The mixture amount is preferably 0 to 30 mol % with respect to the amount of the transition metal. The transition metal oxide obtained by performing mixing and synthesizing such that a molar ratio of Li/$M^a$ becomes 0.3 to 2.2 is more preferable.

[Transition Metal Oxide Represented by Formula (MA) (Laminar Rock Salt Structure)]

For the lithium-containing transition metal oxide, among them, oxides represented by the following formula (MA) are preferable.

$$Li_aM^1O_b \hspace{3cm} (MA)$$

In the formula, $M^1$ has the same meaning as $M^a$ above. a represents 0 to 1.2, preferably 0.1 to 1.15, and further preferably 0.6 to 1.1. b represents 1 to 3 and preferably represents 2. A portion of $M^1$'s may be substituted with the mixture element $M^b$. The transition metal oxide represented by Formula (MA) above typically has a laminar rock salt structure.

Specific examples of the transition metal compound are $LiCoO_2$ (lithium cobalt oxide [LCO]), $LiNi_2O_2$ (lithium nickel oxide), $LiNi_{0.85}Co_{0.10}Al_{0.05}O_2$ (lithium nickel cobalt aluminum oxide [NCA]), $LiNi_{1/3}Co_{1/3}Mn_{1/3}O$, (lithium nickel manganese cobalt oxide [NMC]), and $LiNi_{0.5}Mn_{0.5}O_2$ (lithium manganese nickel oxide).

[Transition Metal Oxide Represented by Formula (MB) (Spinel-Type Structure)]

For the lithium-containing transition metal oxide, among these, a transition metal oxide represented by Formula (MB) below is also preferable.

$$Li_cM^2_2O_d \hspace{3cm} (MB)$$

In the formula, $M^2$ has the same meaning as $M^a$ above. c represents 0 to 2, preferably represents 0.1 to 1.5, more preferably represents 0.6 to 1.5, and even more preferably represents 0.6 to 1.15. d represents 3 to 5, and preferably represents 4.

Specific examples of the transition metal compound are $LiMn_2O_4$ and $LiMn_{1.5}Ni_{0.5}O_4$.

Preferable examples of the transition metal oxide represented by Formula (MB) include the following.

(a) $LiCoMnO_4$
(b) $Li_2FeMn_3O_8$
(c) $Li_2CuMn_3O_8$
(d) $Li_2CrMn_3O_8$
(e) $Li_2NiMn_3O_8$

In view of a high capacity and a high output, among the above, an electrode including Ni is further preferable.

[Transition Metal Oxide Represented by Formula (MC)]

It is preferable that lithium-containing transition metal phosphorus oxides are used as the lithium-containing transition metal oxide. Among them, phosphorus oxides represented by Formula (MC) below are preferable.

$$Li_eM^3(PO_4)_f \hspace{3cm} (MC)$$

In the formula, e represents 0 to 2, preferably represents 0.1 to 1.5, more preferably represents 0.5 to 1.5, and particularly preferably represents 0.5 to 1.15. f represents 0.5 to 5 and preferably represents 0.5 to 2, or 1 to 5.

$M^3$ above represents one or more elements selected from V, Ti, Cr, Mn, Fe, Co, Ni, and Cu. $M^3$ above may be substituted with another metal such as Zn, Zr, and Nb, in addition to the mixture element $M^b$. Specific examples thereof include an olivine-type iron phosphate salt such as $LiFePO_4$ and $Li_3Fe_2(PO_4)_3$, iron pyrophosphates such as $LiFeP_2O_7$, cobalt phosphates such as $LiCoPO_4$, and a monoclinic nasicon-type vanadium phosphate salt such as $Li_3V_2(PO_4)_3$ (lithium vanadium phosphate).

a, c, and e values above indicating the composition of Li are values that change according to charging and discharging and are typically evaluated as values in a stable state when Li is contained. In Formulae (a) to (e) above, as specific values, the composition of Li is indicated, but this also changes according to an operation of the battery.

As particularly preferable specific examples of the cathode active material, the following are provided.

$LiNi_{1/3}Co_{1/3}Mn_{1/3}O_2$
$LiNi_{0.6}Co_{0.2}Mn_{0.2}O_2$
$LiNi_{0.5}Co_{0.3}Mn_{0.2}O_2$
$LiNi_{0.5}Mn_{0.5}O_2$
$LiNi_{0.5}Mn_{1.5}O_4$

Since these can be used at a high potential, these are particularly preferable because battery capacity can be increased, and a capacity retention rate is high even if the battery is used at a high potential.

In the nonaqueous secondary battery according to the invention, the average particle diameter of the cathode active material used is not particularly limited, but is preferably 0.1 to 50 μm. The specific surface area is not particularly limited, but is preferably 0.01 m²/g to 50 m²/g in the BET method. In addition, when 5 g of a cathode active material is dissolved in 100 ml of distilled water, the pH of a supernatant is preferably 7 to 12.

The content of the cathode active material is not particularly limited, but is preferably 60% to 98% by mass and more preferably 70% to 95% by mass with respect to 100% by mass of a solid component in the dispersoid (combination) for configuring an active material layer.

Anode Active Material

As the anode active material, a material that can reversibly insert and discharge lithium ions is preferable, but the anode active material is not particularly limited, and examples thereof include a carbonaceous material, a metal oxide such as tin oxide or silicon oxide, a metal composite oxide, a single substance of lithium, a lithium alloy such as a lithium-aluminum alloy, and a metal that can form an alloy with lithium such as Sn or Si.

These can be used singly or two or more types thereof may be used together in an arbitrary combination or an arbitrary ratio. Among these, a carbonaceous material or a lithium composite oxide is preferably used, in view of reliability.

A metal composite oxide is preferable since a metal composite oxide can occlude or discharge lithium, and it is preferable that titanium and/or lithium is contained as a configurational component, in view of charging and discharging characteristics at a high current density.

The carbonaceous material that is used as the anode active material is a material that is substantially formed of carbon. Examples thereof include artificial graphite such as a petroleum pitch, natural graphite, vapor phase growth graphite, and a carbonaceous material obtained by baking various synthetic resins such as a polyacrylonitrile-based resin or furfuryl alcohol resin. Examples thereof further include various carbon fibers such as a polyacrylonitrile-based carbon fiber, a cellulose-based carbon fiber, a pitch-based carbon fiber, a vapor phase growth carbon fiber, a dehydration polyvinyl alcohol-based carbon fiber, a lignin carbon fiber, a glassy carbon fiber, and an active carbon fiber, mesophase microspheres, a graphite whisker, and flat plate-shaped graphite.

As the metal oxide and the metal composite oxide, an amorphous oxide is particularly preferable, and further a chalcogenide which is a reaction product of a metal element and an element in Group 16 in the periodic table is also preferably used. Specific examples of preferable amorphous oxides and chalcogenides preferably include $Ga_2O_3$, SiO, GeO, SnO, $SnO_2$, PbO, $PbO_2$, $Pb_2O_3$, $Pb_2O_4$, $Pb_3O_4$, $Sb_2O_3$, $Sb_2O_4$, $Sb_2O_5$, $Bi_2O_3$, $Bi_2O_4$, $SnSiO_3$, GeS, SnS, $SnS_2$, PbS, $PbS_2$, $Sb_2S_3$, $Sb_2S_5$, $SnSiS_3$. These may be a composite oxide with lithium oxide, for example, $Li_2SnO_2$.

An average particle size of the anode active material is preferably 0.1 μm to 60 μm.

Examples of the anode active material that can be used together with an amorphous oxide anode active material mainly with Sn, Si, and Ge suitably include a carbon material that can occlude-discharge lithium ions or lithium metal, lithium, a lithium alloy, and metal that can form an alloy with lithium.

In the dispersion (mixture) that forms an electrode composite material, the formulation amount of the anode active material is not particularly limited, and is preferably 60% to 98% by mass and more preferably 70% to 95% by mass with respect to 100% by mass of the solid component.

Conductive Material

The conductive material is preferably an electrically conductive material that does not cause a chemical change in the configured secondary battery, and a well-known conductive material can be arbitrarily used. Generally, conductive materials such as natural graphite (scaly graphite, flaky graphite, earthy graphite, and the like), artificial graphite, carbon black, acetylene black, Ketjen black, a carbon fiber, or metal powder (copper, nickel, aluminum, and silver (disclosed in JP1988-10148A (JP-S63-10148A), JP1988-554A (JP-563-554A), and the like), metal fibers or a polyphenylene derivative (disclosed in JP1984-20971A (JP-559-20971A)) can be included singly or in a mixture. Among these, a combination of graphite and acetylene black is particularly preferable. The addition amount of the conductive material is preferably 1% to 50% by mass and more preferably 2% to 30% by mass. In the case of carbon or graphite, the addition amount thereof is particularly preferably 2% to 15% by mass.

Binding Agent

Examples of the binding agent include polysaccharides, a thermoplastic resin, and a polymer having rubber elasticity. Among these, a polyacrylic acid ester-based latex, carboxymethyl cellulose, polytetrafluoroethylene, and polyvinylidene fluoride are more preferable.

As the binding agent, one kind can be used singly, or two or more types thereof can be used in a mixture. When the addition amount of the binding agent is small, the holding strength and cohesive strength of the electrode composite material are weakened. When the addition amount of the binding agent is excessively great, the electrode volume increases, and thus the capacity per unit volume or unit mass of the electrode is lowered. Due to the above-described reasons, the addition amount of the binding agent is preferably 1% to 30% by mass and more preferably 2% to 10% by mass.

Filler

The electrode composite material may contain a filler. As a material forming the filler, fibrous materials that do not cause a chemical change in the secondary battery according to the invention are preferable in the nonaqueous secondary battery according to the invention. Generally, a fibrous filler formed from an olefin polymer such as polypropylene and polyethylene, and a fibrous filler made of glass, carbon, and the like are used. The addition amount of the filler is not particularly limited, but is preferably 0% to 30% by mass in the dispersoid.

Collector

As collectors of the cathodes and anodes, an electron conductor that does not cause a chemical change in the nonaqueous electrolyte secondary battery according to the invention is preferably used. For the collector of the cathodes, in addition to aluminum, stainless steel, nickel, and titanium, a collector obtained by treating carbon, nickel, titanium, or silver on the surface of aluminum, or stainless steel is preferable. Among these, a collector obtained by treating carbon, nickel, titanium, or silver on the surface of aluminum, or stainless steel is more preferable.

For the collector of the anodes, aluminum, copper, a copper alloy, stainless steel, nickel, or titanium is preferable, and aluminum, copper, or a copper alloy is more preferable.

Regarding the shape of the collector, a film sheet-shaped collector is generally used, but a net-shaped material, a material formed by punching, a lath material, a porous material, foam, a material obtained by molding a group of fibers, and the like can also be used. The thickness of the collector is not particularly limited but is preferably 1 μm to 500 μm. In addition, it is also preferable that the surface of the collector is made to be uneven by a surface treatment.

An electrode composite material of the lithium secondary battery is formed by members appropriately selected from these materials.

(Separator)

The separator that is used in the nonaqueous secondary battery is preferably formed of a material that has mechanical strength, ion permeability, and oxidation-reduction resistance at a contact surface between the cathode and the anode for electrically insulating the cathode and the anode. As such a material, a porous polymer material, an inorganic material, an organic-inorganic hybrid material, or a glass fiber is used. It is preferable that the separator has a shutdown function for securing safety, that is, a function of interrupting the current by blocking pores at 80° C. or higher and increasing resistance, and the blocking temperature is preferably 90° C. to 180° C.

The shape of the pores of the separator is typically circular or elliptical, and the size thereof is 0.05 μm to 30 μm, and preferably 0.1 μm to 20 μm. Further, the shape of the pores may be a rod shape or an undefined shape in the same manner as when a separator is prepared using a stretching method or a phase separation method. An occupancy ratio of the pores, that is, porosity is 20% to 90% and preferably 35% to 80%.

As the polymer material, a single material such as cellulose non-woven fabric, polyethylene, or polypropylene may be used, and a composite material of two or more kinds may be used. A laminate of two or more microporous films of which pore sizes, porosities, and pore blocking temperatures are changed is preferable.

As the inorganic material, an oxide such as alumina or silicon dioxide, a nitride such as aluminum nitride or silicon nitride, or a sulfate such as barium sulfate or calcium sulfate is used, and a material having a particulate form or a fibrous form is used. With respect to the forms of the inorganic material, a thin film-shaped material such as a non-woven fabric, a woven fabric, or a microporous film is used. As the thin film-shaped material, a material having a pore size of 0.01 μm to 1 μm and a thickness of 5 μm to 50 μm is preferably used. In addition to the above-described independent thin film-shaped material, a separator obtained by forming a composite porous layer containing particles of the inorganic material described above on a surface layer of the cathode and/or the anode by using a binding agent formed of a resin can be used. Examples thereof include a separator obtained by forming a porous layer containing alumina particles having a 90% particle diameter of less than 1 μm on both surfaces of the cathode by using a binding agent formed of a fluororesin.

(Manufacturing of Nonaqueous Secondary Battery)

As the shape of the nonaqueous secondary battery according to the invention, any shape such as a sheet shape, a rectangular shape, or a cylindrical shape can be applied. In many cases, the collectors are applied (coated) with the mixture containing the cathode active material or the anode active material, and dried and compressed for use. Selection and designs of respective members and construction of these can be performed in conventional methods and general techniques of these products can be appropriately applied.

EXAMPLES

Hereinafter, the invention is described in detail with reference to examples, but the invention is not construed in a manner of being limited to these examples. In the examples below, parts and % are based on mass.

Example 1

Under a nitrogen flow, 40.0 g (0.16 mol) of hexafluorophosphazene (a product manufactured by Tokyo Chemical Industry Co., Ltd.) and 100 mL of acetonitrile were introduced to a 500 mL three-neck flask, cooling was performed with an ice/methanol bath, and 10.90 g (0.16 mol) of cyclopentene was added. Subsequently, 7.21 g (0.16 mol) of dimethylamine gas (manufactured by Sigma-Aldrich Co., LLC.) was bubbled to a reaction liquid at −10° C. to 0° C. at a speed of 0.3 g/min.

Subsequently, reaction was performed for one hour at room temperature (about 23° C.). The reaction progress state was confirmed in $^{19}$F-NMR, a reaction conversion rate was 85%, and a disubstituted product was not confirmed. Generation of monofluorinated cyclopentane was confirmed.

Figure 2:
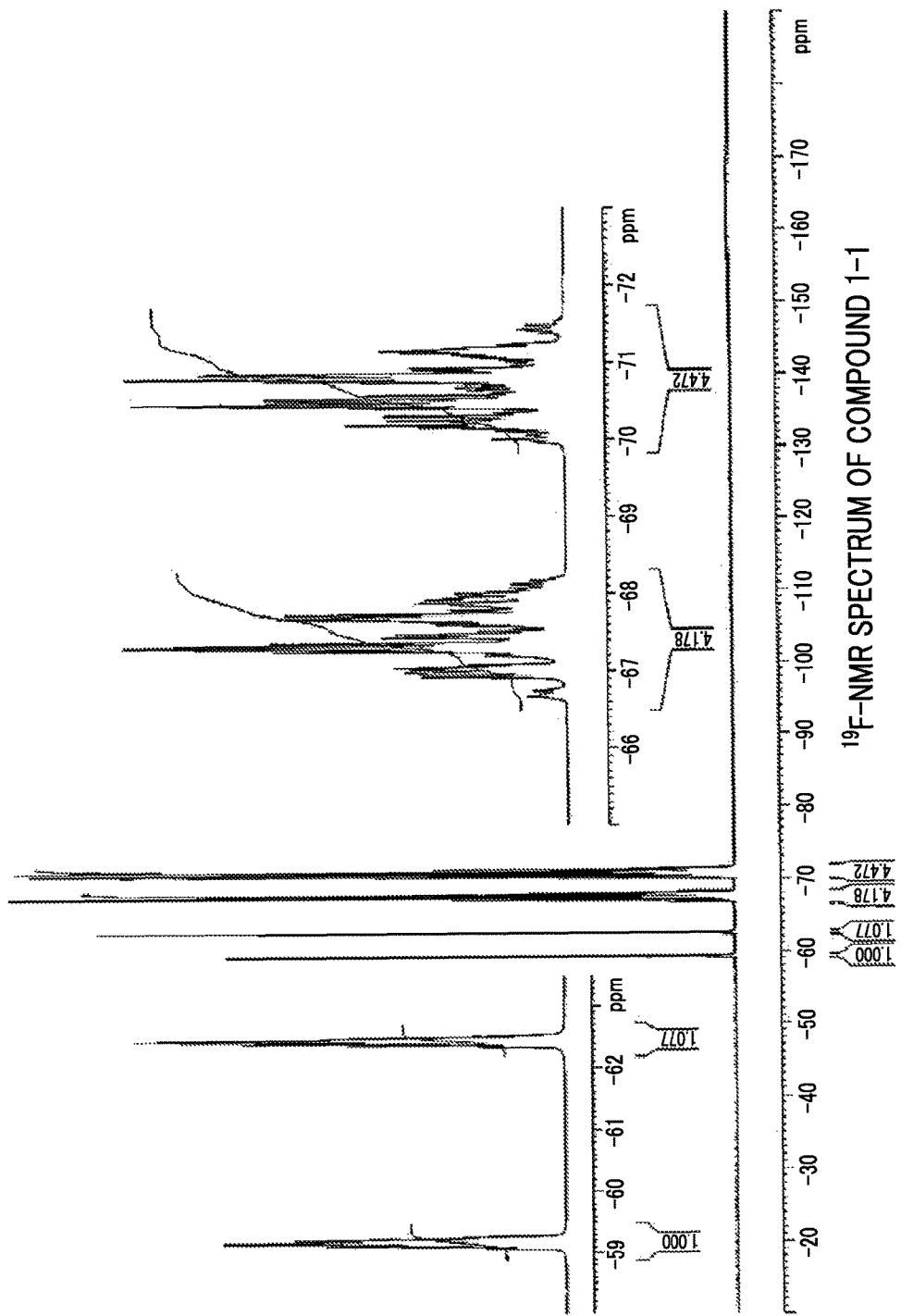
FIG. 2 is a $^{19}$F-NMR spectrum of the compound (1-1).

After the reaction was ended, 33.67 g of the colorless and transparent compound (1-1) was obtained in a yield of 77% by liquid separation and purification and distillation under reduced pressure. $^1$H, $^{19}$F-NMR spectra of the compound (1-1) are illustrated in FIGS. 1 and 2. The purity was confirmed in gas chromatography, and the purity was 99.99% or greater.

Example 2 and the Like

With respect to steps of Example 1, respective reactions were performed by substituting the fluorine trapping agents used as presented in the table below.

Comparative Example 1

Under a nitrogen flow, 40.0 g (0.16 mol) of hexafluorophosphazene (a product manufactured by Tokyo Chemical Industry Co., Ltd.) and 100 mL of acetonitrile were introduced to a 500 mL three-neck flask, while cooling was performed with an ice/methanol bath. Subsequently, 14.41 g (0.32 mol) of dimethylamine gas (manufactured by Sigma-Aldrich Co., LLC.) was bubbled to the suspended reaction liquid at −10° C. to 0° C. at a speed of 0.3 g/min.

Subsequently, reaction was performed for one hour at room temperature (about 23° C.). The reaction progress state was confirmed in $^{19}$F-NMR, a reaction conversion rate to a desired product that is a monosubstituted product was 47%, and 10% of a disubstituted product was generated.

After the reaction was ended, 13.35 g of the colorless and transparent compound (1-1) was obtained in a yield of 30% by liquid separation and purification and distillation under reduced pressure. The purity was confirmed in gas chromatography, and the purity was 99.10%.

Comparative Example 2

Under a nitrogen flow, 40.0 g (0.16 mol) of hexafluorophosphazene (a product manufactured by Tokyo Chemical Industry Co., Ltd.), 16.96 g (0.16 mol) of sodium carbonate, and 200 mL of acetonitrile were introduced to a 500 mL three-neck flask. 7.21 g (0.16 mol) of dimethylamine gas (manufactured by Sigma-Aldrich Co., LLC.) was bubbled at a speed of 0.3 g/min while a temperature was maintained at −10° C. to 0° C. with an ice/methanol bath.

Subsequently, reaction was performed for two hours at room temperature (about 23° C.). The reaction progress state was confirmed in $^{19}$F-NMR by using monofluoride benzene as an internal standard, a reaction conversion rate to a desired product was 50%, and 6% of a disubstituted product was generated. The generation of unidentified by-products was also confirmed.

After the reaction was ended, 18.35 g of the colorless and transparent compound (1-1) was obtained in a yield of 42% by liquid separation and purification and distillation under reduced pressure. The purity was confirmed in gas chromatography, and the purity was 99.11%.

Results thereof are collectively presented in Table 1 below.

TABLE 1

| No. | Phosphazene | Amine | Product | Trapping agent | Addition amount | Reaction temperature | Conversion rate | Selectivity | Yield |
|---|---|---|---|---|---|---|---|---|---|
| ex. 1 | HFP | DMA | 1-1 | I-1a | 1.0 | r.t. | 85% | 100% | 77% |
| ex. 2 | HFP | DMA | 1-1 | I-1g | 1.0 | r.t. | 80% | 95% | 72% |
| ex. 3 | HFP | DMA | 1-1 | I-1i | 0.5 | r.t. | 81% | 97% | 72% |
| ex. 4 | HFP | DMA | 1-1 | I-1m | 1.0 | r.t. | 78% | 94% | 70% |
| ex. 5 | HFP | DMA | 1-1 | I-2d | 1.0 | r.t. | 79% | 95% | 69% |
| ex. 6 | HFP | DMA | 1-1 | I-2f | 1.0 | r.t. | 81% | 98% | 73% |
| ex. 7 | HFP | DMA | 1-1 | II-1a | 1.0 | r.t. | 86% | 100% | 76% |
| ex. 8 | HFP | DMA | 1-1 | II-1f | 0.5 | r.t. | 83% | 100% | 75% |

TABLE 1-continued

| No. | Phosphazene | Amine | Product | Trapping agent | Addition amount | Reaction temperature | Conversion rate | Selectivity | Yield |
|---|---|---|---|---|---|---|---|---|---|
| ex. 9 | HFP | DMA | 1-1 | II-1g | 1.0 | r.t. | 79% | 98% | 70% |
| ex. 10 | HFP | DEA | 1-3 | I-1a | 1.0 | r.t. | 81% | 100% | 71% |
| ex. 11 | HFP | DMA | 1-1 | NaF | 1.5 | r.t. | 72% | 94% | 65% |
| ex. 12 | HFP | DMA | 1-1 | KF | 1.5 | r.t. | 73% | 95% | 64% |
| cex. 1 | HFP | DMA | 1-1 | | | r.t. | 47% | 82% | 30% |
| cex. 2 | HFP | DMA | 1-1 | Na$_2$CO$_3$ | 1.0 | r.t. | 50% | 89% | 42% |

<Abbreviations in Table>
Trapping agent: Compound having fluorine trapping function (fluorine trapping agent)
ex: example
cex: comparative Example
HFP: hexafluorophosphazene
DMA: dimethylamine
DEA: diethylamine
r.t.: room temperature (about 23° C.)
An addition amount means a molar ratio with respect to HFP.
Selectivity in Table 1 represents a generation ratio of a desired substituted product in a reaction system.
Selectivity (%)=[desired substituted product conversion rate/(desired substituted product conversion rate+another substituted product conversion rate)]
The amino-substituted phosphazene compounds obtained in the respective examples were used, and the electrolyte solutions for a nonaqueous secondary battery to which the compound was added were prepared. It was understood that the nonaqueous secondary battery using the electrolyte solution exhibited favorable charging and discharging performance and excellent incombustibility of an electrolyte solution was exhibited by adding the substituted phosphazene compound.
Instead of dimethylamine of Example 1 (ex. 1), the exemplary compounds 1-7, 1-8, and 1-12 were synthesized by using predetermined amine compounds. It was confirmed that desired compounds were able to be obtained with favorable yields and selectivity.
Instead of the fluorine trapping agent (I-1a) of Example 1 (ex. 1), synthesis of the exemplary compound 1-1 was performed by using I-1b, I-1k, I-2g, II-1d, II-1e, or CsF$_2$. It was confirmed that desired compounds were able to be obtained with a favorable yield and selectivity.
The invention has been described in detail with reference to specific embodiments, but, unless otherwise specified, any details of the descriptions are not intended to limit the invention, and it is obvious that the invention may be widely construed without departing from the gist and the scope of the invention recited in the accompanying claims.
This application is based on JP2014-138947 filed on Jul. 4, 2014, and the entire contents thereof are incorporated herein by reference.

What is claimed is:

1. A manufacturing method for an amino-substituted phosphazene compound comprising:
   reacting a fluorinated phosphazene compound and an amine compound in presence of a compound having a fluorine trapping function; and
   synthesizing a compound obtained by substituting the amine compound for the fluorinated phosphazene compound;
   wherein
   the compound having a fluorine trapping function is a compound having a carbon-carbon unsaturated bond, a compound having a bond between silicon and oxygen, and fluoride of alkali metal or alkali earth metal,
   the fluorinated phosphazene compound is represented by Formula (2) below,

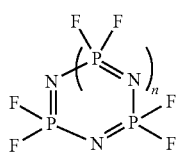

wherein, n represents 1 or 2, and
   the amine compound is represented by H—NR$^1$R$^2$ wherein R$^1$ and R$^2$ each independently represent a monovalent substituent or a hydrogen atom.

2. The manufacturing method according to claim 1,
   wherein the compound having a fluorine trapping function is at least one selected from the group consisting of a compound represented by Formula (I-1) or (I-2) below, a compound represented by Formula (II-1) below, and a metal compound having a structure represented by Formula (III-1) below,

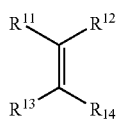

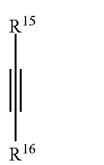

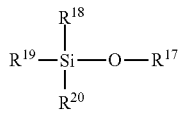

where R$^{11}$R$^{14}$ each independently represent a hydrogen atom, an alkyl group, an alkenyl group, an alkynyl group, an aryl group, an aralkyl group, an alkoxy group, an aryloxy group, an aralkyloxy group, an amino group, a halogen atom, a carbonyl group-containing group, or a cyano group, and R$^{11}$ to R$^{14}$ that are adjacent to each other may form rings,
R$^{15}$ and R$^{16}$ each independently represent an alkyl group, an alkenyl group, an alkynyl group, an aryl group, an aralkyl group, an alkoxy group, an aryloxy group, an aralkyloxy group, an amino group, a halogen atom, a carbonyl group-containing group, or a cyano group, and R$^{15}$ and R$^{16}$ that are adjacent to each other may form a ring,
R$^{17}$ represents an alkyl group, an aryl group, or a carbonyl group-containing group, and R$^{18}$ to R$^{20}$ each independently represent a hydrogen atom, an alkyl group, an alkenyl group, an alkynyl group, an aryl group, an aralkyl group, an alkoxy group, an aryloxy group, an aralkyloxy group, an amino group, a halogen atom, or a carbonyl group-containing group, and M represents Li, Na, K, Cs, or Ca.

3. The manufacturing method according to claim 2, wherein the compound represented by Formula (I-1), (I-2), or (II-1) above is a compound having 2 to 16 carbon atoms.

4. The manufacturing method according to claim 1, wherein the compound having a fluorine trapping function is added to the fluorinated phosphazene compound by 0.25 to 2 equivalents.

5. The manufacturing method according to claim 1, wherein the amino-substituted phosphazene compound is a compound represented by Formula (1) below,

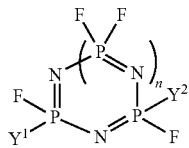

(1)

in the formula, $Y^1$ represents $-NR^1R^2$, $Y^2$ represents a fluorine atom or $-NR^3R^4$, $R^1$ to $R^4$ each independently represent a monovalent substituent or a hydrogen atom, $R^1$ and $R^2$ or $R^3$ and $R^4$ may form a ring, and n represents 1 or 2.

6. The manufacturing method according to claim 1, wherein the number of carbon atoms of the amine compound is 1 to 12.

7. A manufacturing method for an electrolyte solution for a nonaqueous secondary battery, comprising:

preparing an electrolyte solution for a nonaqueous secondary battery containing the amino-substituted phosphazene compound via the manufacturing method according to claim 1.

8. A manufacturing method for a nonaqueous secondary battery, comprising:

manufacturing a nonaqueous secondary battery including a cathode, an anode, and the electrolyte solution for a nonaqueous secondary battery by the manufacturing method according to claim 7.

* * * * *